(12) United States Patent
Beller et al.

(10) Patent No.: US 6,472,570 B1
(45) Date of Patent: Oct. 29, 2002

(54) METHOD FOR THE ASYMMETRIC DIHYDROXYLATION OF OLEFINS, USING OSMIUM CATALYSTS

(75) Inventors: Matthias Beller, Rostock (DE); Christian Döbler, Lichtenhagen-Dorf (DE); Gerald Mehltretter, Rostock (DE); Uta Sundermeier, Rostock (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/980,504

(22) PCT Filed: Apr. 18, 2000

(86) PCT No.: PCT/EP00/03494
§ 371 (c)(1),
(2), (4) Date: Oct. 19, 2001

(87) PCT Pub. No.: WO00/64844
PCT Pub. Date: Nov. 2, 2000

(30) Foreign Application Priority Data

Apr. 25, 1999 (DE) .......................... 199 20 039

(51) Int. Cl.[7] .............................. C07C 33/26
(52) U.S. Cl. .................. 568/811; 549/374; 556/449; 568/46; 568/644; 568/833; 568/844; 568/860
(58) Field of Search ................................ 568/811, 833, 568/844, 860, 644, 46; 556/449; 549/374

(56) References Cited

U.S. PATENT DOCUMENTS

| | | | |
|---|---|---|---|
| 2,769,824 A | 11/1956 | Schneider et al. | 260/397.45 |
| 4,482,763 A | * 11/1984 | Austin | |
| 4,496,778 A | * 1/1985 | Myers | |
| 4,496,779 A | * 1/1985 | Myers | |
| 4,533,772 A | * 8/1985 | Michaelson | |
| 4,871,855 A | * 10/1989 | Marko | |
| 4,965,364 A | * 10/1990 | Marko | |
| 5,260,461 A | 11/1993 | Hartung et al. | 594/447 |

FOREIGN PATENT DOCUMENTS

| WO | 89/06225 | 7/1989 |
|---|---|---|
| WO | 93/17150 | 9/1993 |

OTHER PUBLICATIONS

Asymmetric Dehydroxylation Reactions (month unavailable) 1996, pp. 1009–1023, Diols via Catalytic Dihydroxylation, Matthias Beller, K. Barry Sharpless.
Chem. Rev. (month unavailable) 1994, 94, pp. 2483–2547, Catalytic Asymmertric Dihydroxylation, Harmuth C. Kolb, Michael S. VanNieuwenhze, and K. Barry Sharpless.
Tetrahedron Letters, vol. 32, No. 32, pp. 3965–3968, (month unavailable) 1991, On The Timing of Hydrolysis/Reoxidation in the Osmium–Catalyzed Asymmetric Dihydroxlation of Olefins using Potassium Ferricyanide as the Reoxidant, Yasukazu Ogino, Hou Chen, Hoi–Lun Kwong, and K. Barry Sharpless.
Chem. Eng. News, Jjun. 13, 1994 p. 41, Science/Technology Concentrates.
Berichte Der Deutschen Chemischen Gesellschaft. (month unavailable) 1912, pp. 3329–3336, Redakteur: R. Pschorr. Mitteilnngen. K.A. Hofmann: Sauerstoff–Ubertragung durch Osmiumtetroxyd und aktivierung von Chlorat–Losungen.
The Journal of American Chemical Society, vol. LXXXI 1959, Jul.–Sep. pp. 3173–5014, A study of the Hydroxylation of Olefins and the Reaction of Osmium Teroxide with 1,2–Glycols, Nicholas A. Milas, Joseph H. Trepagnier, John T. Nolan, Jr., and Miltiadis I. Iliopulos.
Journal of the American Chemical Society vol. 98, (month unavailable) 1976, Osmium Catalyzed Vicinal Hydroxylation of Olefins by tert–Butyl Hydroperoxide under Alkaline Conditions, K. Barry Sharpless and Kageyasu Akashi.
The Journal of Organic Chemistry, vol. 46, Jul.–Sep. 1981, pp. 3936–3938, A Greatly Improved Procedure for Ruthenium Tetraoxide Catalyzed Oxidations of Organic Compounds, P. H. J. Carlsen, Tautomu Katsuk, Victor S. Martin and K. Barry Sharpless.
The Journal of Organic Chemistry, vol. 52 (month unavailable) 1987, pp. 689–691, Synthesis fo Diacids and deto Acids by Ruthenium Tetraoxide Catalyzed Oxidation of Cyclic Allylic Alcohols and α,β–Unsaturated Ketones.
Tetahedron Letters, vol. 29. No. 22 pp. 2701–2702, (month unavailable) 1988, Easy and General Method to Synthesize Chiral 2–Hydroxyacid Benzoates, V.S. Martin M.T. Nunez and C.E. Tonn.
The Journal of Organic Chemistry, vol. 53, (month unavailable) 1988, pp. 5185–5187, Regioselective Azide Opening of 2,3–Epoxy Alcohols by [Ti(O–1–Pr)$_2$(N$_3$)$_2$]: Synthesis of α–Amino Acids. Maurice Caron, Paul R. Carlier and K. Barry Sharpless.
Tetrahedron Letters No. 23, pp. 1973–1976 (month available) 1976, An improved Catalytic OsO$_4$ Oxidation of Olefins to CIS–2–Glycols Using Tertiary Amine Oxides as the Oxidant. V. VanRheenen, R.C. Kelly and D.Y. Cha.
K.B. Sharpless, et al.: "The osmium–catalysed asymmetric dihydroxylation: a new ligand class and process improvement" Journal of Organic Chemistry, Bd. 57, Nr. 10, May 8, 1992, Seiten 2768–2771, XP002144279 American Chemical Society, Washington, DC, US ISSN: 0022–3263 das ganze Dokument.

* cited by examiner

Primary Examiner—Michael L. Shippen
(74) Attorney, Agent, or Firm—Joseph C. Gil; Richard E. L. Henderson

(57) ABSTRACT

This invention relates to process for asymmetric dihydroxylation of olefins using osmium catalysts to obtain monofunctional, bifunctional, and/or polyfunctional chiral 1,2-diols of the formula (I)

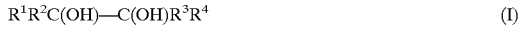

$$R^1R^2C(OH)—C(OH)R^3R^4 \qquad (I)$$

where $R^1$ to $R^4$ are defined herein, by reacting an olefin of the formula (II)

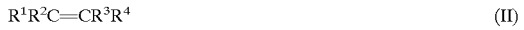

$$R^1R^2C=CR^3R^4 \qquad (II)$$

where $R^1$ to $R^4$ are defined as for formula (I),
with molecular oxygen in the presence of an osmium compound and a chiral amine ligand in water or a water-containing solvent mixture at a pH of from 8.5 to 13.

15 Claims, No Drawings

METHOD FOR THE ASYMMETRIC DIHYDROXYLATION OF OLEFINS, USING OSMIUM CATALYSTS

The present invention relates to a process for preparing chiral 1,2-diols from olefins using catalysts based on osmium compounds. Chiral 1,2-diols are of industrial importance as fine chemicals and as intermediates for pharmaceuticals and for active compounds in the agrochemicals sector.

The standard method of synthesizing chiral 1,2-diols is the Sharpless dihydroxylation reaction in which olefins are reacted in the presence of osmium tetroxide, chiral nitrogen ligands and superstoichiometric amounts of potassium hexacyanoferrate and potassium carbonate as oxidant. Review articles describing this methodology may be found, for example, in "Asymmetric Dihydroxylation Reactions" M. Beller, K. B. Sharpless, in B. Cornils, W. A. Herrmann (Eds.) VCH, 1996, Weinheim, and H. C. Kolb, M. S. Van Nieuwenhze, K. B. Sharpless, Chem. Rev. 1994, 94, 2483.

A critical disadvantage of the Sharpless dihydroxylation is the use of a number of equivalents of potassium hexacyanoferrate as oxidant (Y. Ogino, H. Chen, H. L. Kwong, K. B. Sharpless, *Tetrahedron Lett*. 1991, 32, 3965). Apart from the cost of the oxidant, the formation of large amounts of salt and metal wastes is, in particular, ecologically disadvantageous. Thus, both the price and the superstoichiometric amount of the iron complex to be used (3 mol=990 g per 1 mol of substrate) with addition of potassium carbonate (3 mol=420 g) is a considerable disadvantage in a synthesis of the diols on a relatively industrial scale. Processes for the electrochemical oxidation of the $Na_4[Fe(CN)_6]$ formed in the reaction to $Na_3[Fe(CN)_6]$ (Sepracor Inc. (Y. Gao, C. M. Zepp), PCT Int. Appl. WO 9.317.150, 1994; Anon., *Chem. Eng. News*, 1994, 72 (24), 41) are also difficult to implement on an industrial scale since electrochemical processes are generally too expensive due to the apparatus required.

Although the literature discloses less expensive oxidants for dihydroxylations (for example chlorates; K. A. Hofmann, Chem. 1912, 45, 3329; $H_2O_2$ in tert-butanol: N. A. Milas, J.-H. Trepagnier, J. T. Nolan, M. Ji. Iliopolus, *J. Am. Chem. Soc*. 1959, 81, 4730: tert-butyl hydroperoxide in the presence of $Et_4NOH$; K. B. Sharpless, K. Akashi, *J. Am. Chem. Soc*. 1976, 98, 1986: P. H. J. Carisen, T. Katsuki, V. S. Martin, K. B. Sharpless, *J. Org. Chem*. 1981, 46, 3936; F. X. Webster, J. Rivas-Enterrios, R. M. Silverstein, *J Org. Chem*. 1987, 52, 689; V. S. Martin, M. T. Nunez, C. E. Tonn, *Tetrahedron Lett*. 1988, 29, 2701; M. Caron, P. R. Carlier, K. B. Sharpless, *J Org. Chem*. 1988, 53, 5185, tertiary amine oxides and, in most cases, N-methylmorpholine N-oxide; W. P. Schneider, A. V. Mcintosh, U.S. Pat. No. 2.769.824 (1956); V. Van Rheenen, R. C. Kelly, D. Y. Cha, *Tetrahedron Lett*. 1976, 17, 1973), none of the processes mentioned allow preparation of chiral diols with good enantioselectivities.

To avoid the indicated disadvantages of the known catalytic process using potassium hexacyanoferrate, it is an object of the invention to develop a novel process for asymmetric dihydroxylation which gives chiral 1,2-diols in high yield, enantioselectivity and purity using an inexpensive reoxidant and which is suitable for industrial implementation.

This object is achieved by a process for the asymmetric dihydroxylation of olefins by means of osmium catalysts, in which, according to the invention, monofunctional, bifunctional and/or polyfunctional 1,2-diols of the formula (I)

$$R^1R^2C(OH)-C(OH)R^3R^4 \qquad (I)$$

where $R^1$ to $R^4$ are each, independently of one another, hydrogen, alkyl, CN, COOH, COO-alkyl, COO-aryl, CO-alkyl, CO-aryl, O-alkyl, O-aryl, O-CO-aryl, O-CO-alkyl, OCOO-alkyl, $N$-alkyl$_2$, NH-alkyl, $N$-aryl$_2$, NH-aryl, NO, $NO_2$, NOH, aryl, fluorine, chlorine, bromine, iodine, $NO_2$, Si-alkyl$_3$, CHO, $SO_3H$, $SO_3$-alkyl, $SO_2$-alkyl, SO-alkyl, $CF_3$, NHCO-alkyl, $CONH_2$, CONH-alkyl, NHCOH, NHCOO-alkyl, $CHCHCO_2$-alkyl, $CHCHCO_2H$, PO-(aryl)$_2$, PO-(alkyl)$_2$, $PO_3H_2$, PO(O-alkyl)$_2$, where alkyl represents an aliphatic organic group having from 1 to 18 carbon atoms which may be linear, branched and/or cyclic and aryl is a five-, six- or seven-membered aromatic ring which contains from 4 to 14 carbon atoms and may be fused and contain from 0 to 3 hetero atoms such as N, O, S and where the alkyl and/or the aryl group may bear up to six further substituents selected independently from among hydrogen, alkyl, O-alkyl, OCO-alkyl, O-aryl, aryl, fluorine, chlorine, bromine, iodine, OH, $NO_2$, NO, Si-alkyl$_3$, CN, COOH, CHO, $SO_3H$, $NH_2$, NH-alkyl, $N$-alkyl$_2$, PO-alkyl$_2$, $SO_2$-alkyl, SO-alkyl, $CF_3$, NHCO-alkyl, COO-alkyl, $CONH_2$, CO-alkyl, NHCOH, NHCOO-alkyl, CO-aryl, COO-aryl, PO-aryl$_2$, $PO_3H_2$, PO(O-alkyl)$_2$, $SO_3$-alkyl, where alkyl and aryl are as defined above, are obtained by reacting olefins of the formula (II)

$$R^1R^2C=CR^3R^4 \qquad (II)$$

where $R^1$ to $R^4$ are as defined above, with molecular oxygen in the presence of a catalytic amount of an osmium compound and a chiral amine in water or a water-containing solvent mixture at a pH of from 7.5 to 13.

In particular, compounds of the formula (I) are prepared using olefins of the formula (II) in which the substituents $R^1$ to $R^4$ are each, independently of one another, hydrogen, alkyl, CN, COOH, COO-alkyl, COO-aryl, CO-alkyl, CO-aryl, O-alkyl, O-aryl, N-alkyl$_2$, aryl, fluorine, chlorine, bromine, iodine, CHO, $CF_3$, NHCO-alkyl, $CONH_2$, CONH-alkyl, NHCOO-alkyl. Here, alkyl and aryl are as defined above.

Particular preference is given to a process in which diols of the formula (I) in which $R^1$ to $R^4$ are each, independently of one another, hydrogen, alkyl, CN, COOH, COO-alkyl, CO-alkyl, CO-aryl, O-alkyl, O-aryl, aryl, fluorine, chlorine, bromine, CHO, NHCO-alkyl. Here alkyl and aryl are as defined above.

The process of the invention is carried out in the presence of water. It has been found to be advantageous to use a further organic solvent in addition to the olefin. The process of the invention can also, in the case of various olefins, be carried out in the olefin/water mixture without further solvent. Further solvents used are generally inert organic solvents. Suitable solvents are aliphatic ethers, aromatic or aliphatic hydrocarbons, alcohols and esters, halogenated hydrocarbons, dipolar aprotic solvents such as dialkyl sulfoxides, N,N-dialkylamides of aliphatic carboxylic acids and also mixtures thereof. Preference is given to alcohols, esters and ethers. The aqueous phase used is generally a basic aqueous solution having a pH of from 7.5 to 13. The basic pH of the solution is achieved by addition of a base to the water. In general, it is advantageous to carry out the process in buffered aqueous solutions, preferably at a pH of from 8 to 13. The buffered solution is prepared by addition of known buffers to water.

To enable the diol products to be separated off readily, it is sometimes advantageous to use an aqueous salt solution or buffered aqueous salt solution, for example an aqueous solution of an alkali metal halide or alkaline earth metal halide, as solvent in place of water or buffered aqueous solutions.

The oxidant used in the process of the invention is molecular oxygen or a gas mixture comprising molecular oxygen. Preference is given to gas mixtures comprising at least 15% by volume of oxygen. Particular preference is given to air and oxygen gas having an oxygen content of >95%.

The reaction preferably proceeds at temperatures of from 20 to 150° C. In many cases, it has been found to be useful to employ temperatures of from 30 to 120° C., preferably from 40 to 80° C. The process of the invention can be carried out at atmospheric pressure, e.g. by passing oxygen through the reaction solution. However, a faster reaction rate can be achieved when a superatmospheric pressure of oxygen is employed. The process can be carried out at pressures of up to 200 bar, but is usually carried out at a pressure of not more than 60 bar and preferably in the range from atmospheric pressure to 20 bar.

Chiral ligands used are chiral amines known from the literature (H. C. Kolb, M. S. Van Nieuwenhze', and K. B. Sharpless, *Chem Rev.* 1994, 94, 2483-2547), for example diaminocyclohexane derivatives, substituted diaminoethanes, bispiperazine, bispyrrolidine, bistetrahydropyridine compounds, 1,4-diazabicyclo[2.2.2]octane derivatives, substituted isooxazolidines, in particular (DHQD)$_2$PHAL (hydroquinidine 1,4-phthalazinediyl diether) and (DHQ)$_2$PHAL (hydroquinine 1,4-phthalazinediyl diether) and (DHQ)$_2$Pyr (hydroquinine 2,5-diphenyl-4,6-pyrimidinyl diether).

The osmium catalysts used are generally osmium compounds in the oxidation states +8 and +6. However, it is also possible to use osmium catalyst precursors in low oxidation states. These are converted under the reaction conditions into the catalytically active Os(VIII) and Os(VI) species. As osmium catalysts or catalyst precursors, it is possible to use, for example, $OsO_4$, $K_2Os_2(OH)_4$, $Na_2Os_2(OH)_4$, $Os_3(CO)_{12}$, $OsCl_3$, $H_2OsCl_6$, $[CF_3SO_3Os(NH_3)_5](O_3SCF_3)_2$, $OsO_4$ on vinylpyridine, $Bu^tNOsO_3$.

In the process of the invention, the osmium catalyst is used in catalytic amounts relative to the olefin. In general, use is made of from 0.2 to 0.00001 equivalents, based on olefin, preferably from 0.1 to 0.0001 equivalents and particularly preferably from 0.08 to 0.0005 equivalents.

The ratio of amine to osmium is from 0.01:1 to 1 000:1, preferably from 0.1:1 to 100:1. Particular preference is given to using ratios of amine to osmium of from 1:50 to 50:1.

When using bulky olefins, in particular trisubstituted and tetrasubstituted olefins, it is sometimes advantageous to use a cocatalyst to hydrolyze the osmate ester formed as an intermediate. This cocatalyst is an amide which promotes the hydrolysis, for example a sulfonamide and/or carboxamide. Particular preference is given to the addition of methylsulfonamide.

The cocatalyst is used in an amount of from 0.01 mol % to 10 mol % (based on olefin), preferably from 0.1 to 5 mol %.

The particular advantage of the process of the invention is the use of oxygen or oxygen-containing gases as reoxidant. Despite the comparatively difficult reoxidation process, high enantioselectivities can be achieved. The catalyst productivity can be increased by treating the aqueous catalyst phase which has been used once with olefin again. In this way, the catalyst costs for the process of the invention are minimized, so that even industrial processes can be carried out economically.

The process of the invention is particularly surprising and novel since no asymmetric osmium-catalyzed dihydroxylation reactions to form 1,2-diols using oxygen as reoxidant were known in the past. The novel combination described in the process of the invention of addition of a ligand which accelerates the dihydroxylation and carrying out the process in a strongly basic buffered solution surprisingly leads to an enantioselective dihydroxylation process even in the presence of oxygen. The process of the invention demonstrates for the first time that the statements made in the known literature in respect of osmium-catalyzed dihydroxylation using oxygen are wrong.

The particular advantages of the novel process are the price advantage of the oxidant, the simplicity of the procedure and the high selectivity of the process compared to known processes using potassium hexacyanoferrate.

The chiral 1,2-diols prepared according to the invention can be used, inter alia, as precursors for agrochemicals, cosmetics, pharmaceuticals and chiral polymers.

The following examples illustrate the process of the invention without restricting it to the examples presented.

EXAMPLES

Example 1

18.4 mg of $K_2OsO_4 \times 2H_2O$ (0.05 mmol) are weighed into a Schlenk vessel. While stirring by means of a magnetic stirrer, 25 ml of 0.4-0.5 molar $Na_3PO_4/Na_2HPO_4$ buffer solution having a pH of 11.2 and 10 ml of 2-methyl-2-propanol are added thereto, resulting in formation of 2 phases. The vessel is heated to 50° C. on a water bath and flushed with oxygen. After addition of 173 $\mu$l of styrene (1.5 mmol), the reaction vessel is connected to a burette filled with oxygen and the reaction solution is stirred at 50° C. under a slightly superatmospheric $O_2$ pressure (about 50 cm of water) for 24 hours.

The reaction mixture is worked up as described below:

2 g of sodium bisulfite and 10 ml of ethyl acetate are added to the reaction solution. After stirring for 10 minutes, the upper organic phase is separated off and the aqueous phase is shaken with 10 ml of ethyl acetate. The organic phases are combined, dried over anhydrous sodium sulfate and evaporated to dryness on a rotary evaporator.

This gives 130 mg of(R)/(S)-1-phenyl-1,2-ethanediol, 63%.

To isolate any acidic product formed, the aqueous solution is acidified and shaken twice with 15 ml each time of ether. This gives 20 mg of a crystalline product of which more than 90% is made up by benzoic acid.

Example 2

The procedure of example 1 is repeated with 7.8 mg (0.01 mmol) of (DHQD)$_2$PHAL (hydroquinidine 1,4-phthalazinediyl diether) being added to the osmium salt. This gives 155 mg of (R)-(+)-1-phenyl-1,2-ethanediol (75%), ee 65% (HPLC), and 30 mg of benzoic acid.

Example 3

18.4 mg of $K_2OsO_4 \times 2H_2O$ (0.05 mmol) and 7.8 mg (0.01 mmol) of (DHQD)$_2$PHAL are weighed into a Schlenk vessel. While stirring by means of a magnetic stirrer, 25 ml of a 0.3 molar borax/NaOH buffer solution having a pH of 2,4 g of NaCl and 10 ml of 2-methyl-2-propanol are added, resulting in formation of 2 phases. The vessel is heated to 50° C. on a water bath and flushed with oxygen. After addition of 288 µl of styrene (2.5 mmol), the reaction vessel is connected to a burette filled with oxygen, and the reaction solution is stirred at 50° C. under a slightly superatmospheric $O_2$ pressure (about 50 cm of water) for 24 hours. The reaction mixture is worked up as described in example 1.

This gives 200 mg of (R)-(+)-1-phenyl-1,2-ethanediol (58%), ee 82% (HPLC), and 40 mg of benzoic acid.

Example 4

1.5 mmol of styrene are reacted with 18.4 mg of $K_2OsO_4 \times 2H_2O$ (0.05 mmol) and 7.8 mg (0.01 mmol) of $(DHQD)_2$PHAL as described in example 1, but the reaction temperature was 30° C. and the reaction time was 62 hours.

After work-up, this gives 107 mg of predominantly (R)-(+)-1-phenyl-1,2-ethanediol (52%), ee 71% (HPLC), and 40 mg of benzoic acid.

Example 5

18.4 mg of $K_2OsO_4 \times 2H_2O$ (0.05 mmol) are reacted with 1.5 mmol of styrene as described in example 1. Prior to the addition of styrene, 8.8 mg (0.01 mmol) of $(DHQ)_2$Pyr (hydroquinine 2,5-diphenyl-4,6-pyrimidinyl diether) are added. This gives 141 mg of predominantly (S)-(−)-1-phenyl-1,2-ethanediol (68%), ee 23% (HPLC), and 40 mg of benzoic acid.

Example 6

Using the procedure of example 1, 231 mg of 2-vinylnaphthalene (1.5 mmol) as substrate are reacted with 18.4 mg of $K_2OsO_4 \times 2H_2O$ (0.05 mmol) with addition of 7.8 mg (0.01 mmol) of $(DHQ)_2$PHAL (hydroquinine 1,4-phthalazinediyl diether). As a difference from example 1, the reaction time was 7 hours. After work-up, this gives 227 mg of (S)-1-(2-naphthyl)-1,2-ethanediol (80%), ee 82% (HPLC). 34 mg of a crystalline product consisting predominantly of 2-naphthalenecarboxylic acid are obtained from the ether solution.

Example 7

Using a method analogous to example 1, 18.4 mg of $K_2OsO_4 \times 2H_2O$ (0.05 mmol) are reacted with 195 µl (1.5 mmol) of α-methylstyrene with addition of 7.8 mg (0.01 mmol) of $(DHQ)_2$PHAL in the 2-phase system indicated.

After work-up in the manner described, this gives 180 mg of predominantly (S)-2-phenyl-1,2-propanediol (79%), ee 60% (GC).

Example 8

Using a method analogous to example 1, 18.4 mg of $K_2OsO_4 \times 2H_2O$ (0.05 mmol) are reacted with 130 µl (1 mmol) of trans-β-methylstyrene with addition of 7.8 mg (0.01 mmol) of $(DHQD)_2$PHAL.

After the usual work-up, this gives 126 mg of (R,R)-1-phenyl-1,2-propanediol (80%).

Example 9

7.4 mg of $K_2OsO_4 \times 2H_2O$ (0.02 mmol) are weighed into a Schlenk vessel. While stirring by means of a magnetic stirrer, 25 ml of a buffer solution having a pH of 10.4 and prepared from 0.5 molar $K_2HPO_4$ solution and 2 molar NaOH, together with 10 ml of 2-methyl-2-propanol are added, resulting in formation of 2 phases. The vessel is heated to 50° C. on a water bath and flushed with oxygen. After addition of 230 µl of styrene (2 mmol), the reaction vessel is connected to a burette filled with oxygen and the reaction solution is stirred at 50° C. under a slightly superatmospheric $O_2$ pressure (about 50 cm of water) for 24 hours.

The reaction mixture is worked up as described below.

2 g of sodium bisulfite and 20 ml of ethyl acetate are added to the reaction solution. After stirring for 10 minutes, the upper organic phase is separated off. Dialcohol and unreacted olefin are determined by means of GC.

Yield of 1-phenyl-1,2-ethanediol: 43% (selectivity: 57%).

Example 10

The procedure of example 9 is repeated, but 0.02 mmol of $(DHQD)_2$PHAL is added to the osmium salt.

Yield of (R)-1-phenyl-1,2-ethanediol: 49% (selectivity: 74%), ee 89% (HPLC).

Example 11

The procedure of example 9 is repeated, but 0.06 mmol of $(DHQD)_2$PHAL is added. 308 mg of 2-vinylnaphthalene (2 mmol) are used as substrate; dialcohol and unreacted olefin are in this case determined by means of HPLC.

Yield of (R)-1-(2-naphthyl)-1,2-ethanediol: 55% (selectivity: 76%), ee 93% (HPLC).

Example 12

As described in example 9, but a buffer solution of pH=11.2 is used and 7.4 mg of $K_2OsO_4 \times 2H_2O$ (0.02 mmol)/0.06 mmol of $(DHQD)_2$PHAL are reacted with 318 µl of 1-phenyl-1-cyclohexene (2 mmol).

Yield of (1R,2R)-1-phenyl-1,2-cyclohexanediol: 80% (selectivity: 83%), ee 90% (HPLC).

Example 13

As described in example 9, but 3.7 mg of $K_2OsO_4 \times 2H_2O$ (0.01 mmol)/0.03 mmol of $(DHQD)_2$PHAL are reacted with 260 µl of α-methylstyrene (2 mmol) over a reaction time of 19 hours.

Yield of (R)-2-phenyl-1,2-propanediol: 96% (selectivity: 96%), ee 81% (GC).

Example 14

The procedure of example 13 is repeated using $(DHQD)_2$PYR (hydroquinidine 2,5-diphenyl-4,6-pyrimidinediyl diether) as ligand.

Yield of (R)-2-phenyl-1,2-propanediol: 95% (selectivity: 95%), ee 43% (GC).

Example 15

The procedure of example 13 is repeated using $(DHQD)_2$AQN (hydroquinidine anthraquinone-1,4-diyl diether) as ligand.

Yield of (R)-2-phenyl-1,2-propanediol: 96% (selectivity: 96%), ee 65% (GC).

Example 16

The procedure of example 13 is repeated using 0.006 mmol of $(DHQD)_2$PHEN (hydroquinidine 9-phenanthryl ether) as ligand.

Yield of (R)-2-phenyl-1,2-propanediol: 94% (selectivity: 96%), ee 42% (GC).

Example 17

Using a method analogous to example 13, 1-octene is reacted over a reaction time of 15 hours.

Yield of (R)-1,2-octanediol: 98% (selectivity: 99%), ee 65% (HPLC, bisbenzoate).

Example 18

As described in example 9, but 7.4 mg of $K_2OsO_4 \times 2H_2O$ (0.02 mmol)/0.06 mmol of $(DHQD)_2PHAL$ are reacted with 240 µl of 1-methyl-1-cyclohexene (2 mmol) over a reaction time of 12 hours using a buffer solution having a pH of 11.2.

Yield of (1R,2R)-1-methyl-1,2-cyclohexanediol: 82% (selectivity: 85%), ee 49% (HPLC, bisbenzoate).

Example 19

Method analogous to example 9, but 320 µl of allyltrimethylsilane (2 mmol) are reacted over a reaction time of 6 hours.

Yield of (S)-3-trimethylsilyl- 1,2-propanediol: 79% (selectivity: 89%), ee 15% (HPLC, bisbenzoate).

Example 20

As described in example 9, but 14.7 mg of $K_2OsO_4 \times 2H_2O$ (0.04 mmol)/0.12 mmol of $(DHQD)_2PHAL$ are reacted with 380 µl of trans-5-decene (2 mmol) over a reaction time of 18 hours using a buffer solution having a pH of 12.0.

Yield of (R,R)-5,6-decanediol: 95% (selectivity: 98%), ee 88% (HPLC, bisbenzoate).

Example 21

Using a method analogous to example 20, 245 µl of 2-methyl-2-pentene (2 mmol) are reacted at pH=11.2.

Yield of (2R,3R)-2-methyl-2,3-pentanediol: 88% (selectivity: 87%), ee 87% (HPLC, bisbenzoate).

Example 22

Using a method analogous to example 20, 240 µl of 2-vinyl-1,3-dioxolane (2 mmol) are reacted at pH=10.4.

Yield of (S)-2-(1,2-dihydroxyethyl)-1,3-dioxolane: 63% (selectivity: 86%), ee 23% (HPLC, bisbenzoate).

Example 23

Using a method analogous to example 22, 692 mg of 1H,1H,2H-perfluoro-1-octene (2 mmol) are reacted using $(DHQD)_2AQN$ as ligand.

Yield of 1H,1H,2H-perfluorooctane-1,2-diol: 40% (selectivity: 83%), ee 45% (HPLC, bisbenzoate).

Example 24

7.4 mg of $K_2OsO_4 \times 2H_2O$ (0.02 mmol)/0.06 mmol of $(DHQD)_2PHAL$ are reacted with 275 ml of allyl phenyl ether (2 mmol) over a reaction time of 18 hours as described in example 9.

Yield of (S)-3-phenoxy-1,2-propanediol: 80% (selectivity: 95%), ee 74% (HPLC).

Example 25

Using a method analogous to example 24, 295 µl of allyl phenyl sulfide (2 mmol) are reacted using $(DHQD)_2AQN$ as ligand.

Yield of (S)-(2,3-dihydroxypropyl) phenyl sulfide: 67% (selectivity: 92%), ee 63% (HPLC).

Example 26

0.002 mmol of $K_2OsO_4 \times 2H_2O$ dissolved in water, 0.030 mmol of $(DHQD)_2PHAL$ and 25 ml of buffer solution having a pH of 10.4 and prepared from 0.5 molar $K_2HPO_4$ solution and 2 molar NaOH, together with 12 ml of 2-methyl-2-propanol are placed in a glass vessel located in a pressure autoclave, and the mixture is stirred by means of a magnetic stirrer. 2 phases are formed. After addition of 260 µl of α-methylstyrene (2 mmol), the autoclave is pressurized with 3 bar of oxygen and is heated to 50–55° C.

After 24 hours, the reaction mixture is worked up as described in example 9.

Yield of (R)-2-phenyl-1,2-propanediol: 93% (selectivity: 93%), ee 78% (GC).

Example 27

0.001 mmol of $K_2OsO_4 \times 2H_2O$/0.015 mmol of $(DHQD)_2$PHAL are reacted with 260 µl of a-methylstyrene (2 mmol) at an $O_2$ pressure of 5 bar as described in example 26.

Yield of (R)-2-phenyl- 1,2-propanediol: 94% (selectivity: 94%), ee 77% (GC).

Example 28

The procedure of example 26 is repeated, but the autoclave is pressurized with 8 bar of compressed air in place of pure oxygen.

Yield of (R)-2-phenyl-1,2-propanediol: 80% (selectivity: 93%), ee 80% (GC).

What is claimed is:

1. A process for the asymmetric dihydroxylation of olefins using osmium catalysts to prepare monofunctional, bifunctional and/or polyfunctional chiral 1,2-diols of the formula (I)

$$R^1R^2C(OH)\text{—}C(OH)R^3R^4 \qquad (I)$$

where $R^1$ to $R^4$ are each, independently of one another, hydrogen, alkyl, CN, COOH, COO-alkyl, COO-aryl, CO-alkyl, CO-aryl, O-alkyl, O-aryl, O—CO-aryl, O—CO-alkyl, OCOO-alkyl, N-alkyl$_2$, NH-alkyl, N-aryl$_2$, NH-aryl, NO, NO$_2$, NOH, aryl, fluorine, chlorine, bromine, iodine, Si-alkyl$_3$, CHO, SO$_3$H, SO$_3$-alkyl, SO$_2$-alkyl, SO-alkyl, CF$_3$, NHCO-alkyl, CONH$_2$, CONH-alkyl, NHCOH, NHCOO-alkyl, CHCHCO$_2$-alkyl, CHCHCO$_2$H, PO-(aryl)$_2$, PO(alkyl)$_2$, PO$_3$H$_2$, or PO(O-alkyl)$_2$, where alkyl is a linear, branched, and/or cyclic aliphatic organic group having from 1 to 18 carbon atoms and aryl is a five-, six-, or seven-membered aromatic ring containing from 4 to 14 carbon atoms and from 0 to 3 heteroatoms and is optionally fused, and where the alkyl and/or the aryl group optionally bears up to six substituents selected independently from the group consisting of hydrogen, alkyl, O-alkyl, OCO-alkyl, O-aryl, aryl, fluorine, chlorine, bromine, iodine, OH, NO$_2$, NO, Si-alkyl$_3$, CN, COOH, CHO, SO$_3$H, NH$_2$, NH-alkyl, N-alkyl$_2$, PO-alkyl$_2$, SO$_2$-alkyl, SO-alkyl, CF$_3$, NHCO-alkyl, COO-alkyl, CONH$_2$, CO-alkyl, NHCOH, NHCOO-alkyl, CO-aryl, COO-aryl, PO-aryl$_2$, PO$_3$H$_2$, PO(O-alkyl)$_2$, and SO$_3$-alkyl, where alkyl and aryl are as defined above, comprising reacting an olefin of the formula (II)

$$R^1R^2C=CR^3R^4 \quad (II)$$

where $R^1$ to $R^4$ are defined as for formula (I),
with molecular oxygen in the presence of an osmium compound and a chiral amine ligand in water or a water-containing solvent mixture at a pH of from 8.5 to 13.

2. The process according to claim 1 for preparing compounds of the formula (I) wherein for olefins of the formula (II) the substituents $R^1$ to $R^4$ are each, independently of one another, hydrogen, alkyl, CN, COOH, COO-alkyl, COO-aryl, CO-alkyl, CO-aryl, O-alkyl, O-aryl, N-alkyl$_2$, aryl, fluorine, chlorine, bromine, iodine, CHO, CF$_3$, NHCO-alkyl, CONH$_2$, CONH-alkyl, or NHCOO-alkyl.

3. The process according to claim 1 wherein chiral diols of the formula (I) in which $R^1$ to $R^4$ are each, independently of one another, hydrogen, alkyl, CN, COOH, COO-alkyl, CO-alkyl, CO-aryl, O-alkyl, O-aryl, aryl, fluorine, chlorine, bromine, CHO, or NHCO-alkyl are prepared.

4. The process according to claim 1 wherein the reaction medium comprises an aqueous solution, the olefin, and an organic solvent.

5. The process according to claim 1 wherein the solvent comprises one or more organic solvents selected from the group consisting of aliphatic ethers, aromatic and aliphatic hydrocarbons, alcohols, and esters, halogenated hydrocarbons, dipolar aprotic solvents, and mixtures thereof.

6. The process according to claim 5 wherein the dipolar aprotic solvent is a dialkyl sulfoxide or a N,N-dialkylamide of an aliphatic carboxylic acid.

7. The process according to claim 1 wherein the oxidant is oxygen or a gas mixture comprising at least 15% by volume of oxygen.

8. The process according to claim 1 wherein the reaction proceeds at a temperature of from 20 to 150° C. and a pressure of up to 200 bar.

9. The process according to claim 1 wherein the chiral amine is a chiral diaminocyclohexane derivative, substituted diaminoethane, bispiperazine, bispyrrolidone, or bistetrahydropyridine compound, 1,4-diazabicyclo[2.2.2]octane derivative, or substituted isooxazolidine.

10. The process according to claim 1 wherein the chiral amine is chiral hydroquinidine 1,4-phthalazinediyl diether, hydroquinine 1,4-phthalazinediyl diether, or hydroquinine 2,5-diphenyl-4,6-pyrimidinyl diether.

11. The process according to claim 1 wherein a sulfonamide is added as a cocatalyst.

12. The process according to claim 11 wherein the sulfonamide cocatalyst is a methylsulfonamide and/or a carboxamide.

13. The process according to claim 1 wherein one or more of the osmium compounds OsO$_4$, K$_2$OsO$_2$(OH)$_4$, Na$_2$Os$_2$(OH)$_4$, Os$_3$(CO)$_{12}$, OsCl$_3$, H$_2$OsC$_6$, [CF$_3$SO$_3$Os(NH$_3$)$_5$](O$_3$SCF$_3$)$_2$, OsO$_4$ on vinylpyridine, or Bu$^t$NOsO$_3$ are used as catalysts and/or catalyst precursors.

14. The process according to claim 1 wherein the osmium catalyst is used in amounts of from 0.2 to 0.00001 equivalents, based on the olefin.

15. The process according to claim 1 wherein the ratio of amine to osmium is from 0.01:1 to 1 000:1.

* * * * *